US007709523B2

(12) United States Patent
Salvati et al.

(10) Patent No.: US 7,709,523 B2
(45) Date of Patent: May 4, 2010

(54) ALPHA-AMINOAMIDE DERIVATIVES USEFUL AS ANTIMIGRAINE AGENTS

(75) Inventors: Patricia Salvati, Arese (IT); Marcello Calabresi, Cardano (IT); Luciano Dho, Parabiago (IT); Orietta Veneroni, Milan (IT); Piero Melloni, Bresso (IT)

(73) Assignee: Newron Pharmaceuticals SpA, Bresso (Mi) (IT)

( * ) Notice: Subject to any disclaimer, the term of this patent is extended or adjusted under 35 U.S.C. 154(b) by 696 days.

(21) Appl. No.: 10/541,195

(22) PCT Filed: Nov. 18, 2003

(86) PCT No.: PCT/EP03/12889

§ 371 (c)(1),
(2), (4) Date: Jun. 30, 2005

(87) PCT Pub. No.: WO2004/062655

PCT Pub. Date: Jul. 29, 2004

(65) Prior Publication Data
US 2006/0079570 A1 Apr. 13, 2006

(30) Foreign Application Priority Data
Jan. 16, 2003 (EP) .................................. 03000921

(51) Int. Cl.
*A61K 31/381* (2006.01)
*A61K 31/165* (2006.01)
*A61P 25/06* (2006.01)

(52) U.S. Cl. ........................ 514/447; 514/620; 514/617; 514/666; 514/667; 514/676; 514/678; 514/706; 514/717

(58) Field of Classification Search ................. 514/447, 514/620, 617, 666, 667, 675, 676, 678, 706, 514/717
See application file for complete search history.

(56) References Cited

U.S. PATENT DOCUMENTS

| 3,549,690 A | 12/1970 | Leigh et al. |
| 3,576,864 A | 4/1971 | Nagarajan |
| 3,658,967 A | 4/1972 | Leigh et al. |
| 4,049,663 A | 9/1977 | Harper et al. |
| 4,267,354 A | 5/1981 | Krapcho et al. |
| 4,311,853 A | 1/1982 | Cree et al. |
| 4,513,009 A | 4/1985 | Roques et al. |
| 4,631,287 A | 12/1986 | Chakraborty et al. |
| 4,639,468 A | 1/1987 | Roncucci et al. |
| 4,725,608 A | 2/1988 | Nakaguchi et al. |
| 4,725,619 A | 2/1988 | Chakraborty et al. |
| 4,839,369 A | 6/1989 | Youssefyeh et al. |
| 4,927,835 A | 5/1990 | Kise et al. |
| 4,927,836 A | 5/1990 | Holloway et al. |
| 5,236,957 A | 8/1993 | Dostert et al. |
| 5,391,577 A | 2/1995 | Dostert et al. |
| 5,446,066 A | 8/1995 | Varasi et al. |
| 5,449,692 A | 9/1995 | Varasi et al. |
| 5,475,007 A | 12/1995 | Cai et al. |
| 5,482,964 A | 1/1996 | Hays |
| 5,498,610 A | 3/1996 | Chenard |
| 5,502,079 A | 3/1996 | Dostert et al. |
| 5,670,546 A | 9/1997 | Park et al. |
| 5,688,830 A | 11/1997 | Berger et al. |
| 5,723,489 A | 3/1998 | Sher et al. |
| 5,741,818 A | 4/1998 | Dimmock |
| 5,849,737 A | 12/1998 | Chaplan et al. |
| 5,945,454 A | 8/1999 | Peverello et al. |
| 6,281,211 B1 | 8/2001 | Cai et al. |
| 6,303,819 B1 | 10/2001 | Peverello et al. |
| 6,479,484 B1 | 11/2002 | Lan et al. |
| 6,500,825 B2 | 12/2002 | Lan et al. |
| 7,091,210 B2 | 8/2006 | Lan et al. |
| RE40,259 E | 4/2008 | Pevarello et al. |
| 2007/0093495 A1 | 4/2007 | Ruggero et al. |
| 2007/0203182 A1 | 8/2007 | Besana et al. |
| 2008/0096965 A1 | 4/2008 | Barbanhti et al. |

FOREIGN PATENT DOCUMENTS

| EP | 0415143 A1 | 3/1991 |
| EP | 0 525 360 A2 | 2/1993 |
| EP | 0200101 A2 | 12/1996 |
| EP | 1 123 702 A1 | 8/2001 |
| GB | 1140748 | 1/1969 |
| GB | 2059963 A | 4/1981 |
| WO | WO 90/14334 | 11/1990 |

(Continued)

OTHER PUBLICATIONS

Gallagher et al., "Migraine: Diagnosis, Management, and New Treatment Options", American Journal of Managed Care, 2002, 8, S58-S73.*

Strittmatter et al., "Cerebrospinal Fluid Neuropeptides and Monoaminergic Transmitters in Patients With Trigeminal Neuralgia", Headache 1997, 37, pp. 211-216.*

Goadsby et al., "The trigeminovascular system and migraine: studies characterizing cerebrovascular and neuropeptide changes seen in humans and cats.", Ann Neurol. 1993, 33(1), pp. 48-56.*

Pietrobon et al., 2003, "Neurobiology of Migraine," *Nature Reviews Neuroscience*, vol. 4, 386-398.

(Continued)

*Primary Examiner*—Sreeni Padmanabhan
*Assistant Examiner*—Sahar Javanmard
(74) *Attorney, Agent, or Firm*—Dechert LLP

(57) ABSTRACT

α-Aminoamide derivatives useful as antimigraine agents, particularly for the treatment of head pain conditions such as migraine, cluster headache or other severe headache, are disclosed. The antimigraine agents of the invention are able to reduce or even stop the pain deriving from such conditions without, virtually, any side effects.

16 Claims, No Drawings

FOREIGN PATENT DOCUMENTS

| WO | WO 94/22808 | 10/1994 |
|----|----|----|
| WO | WO 94/22809 | 10/1994 |
| WO | WO 96/40628 | 12/1996 |
| WO | WO 97/05102 | 2/1997 |
| WO | WO 97/05111 | 2/1997 |
| WO | WO 98/19998 | 5/1998 |
| WO | WO 98/25594 | 6/1998 |
| WO | WO 98/43964 | 10/1998 |
| WO | WO 98/47869 | 10/1998 |
| WO | 99 26614 A1 | 6/1999 |
| WO | WO 99/26614 | 6/1999 |
| WO | 99 35125 A1 | 7/1999 |
| WO | WO 99/35123 | 7/1999 |
| WO | WO 99/35125 | 7/1999 |
| WO | WO 99/39712 | 8/1999 |
| WO | WO 00/61188 | 10/2000 |

OTHER PUBLICATIONS

Bolay et al., 2002, "Intrinsic Brain Activity Triggers Trigeminal Meningeal Afferents in a Migraine Model," *Nature Medicine*, vol. 8, No. 2, 136-142.

Anonymous, "Cambridge NeuroScience's grant for channel blockers," *SCRIP World Pharmaceutical News* 1870:8 (1993).

Anonymous, "Neurogen Licenses National Institutes of Health (NIH) anticonvulsants," *SCRIP World Pharmaceutical News* 1773:14 (1992).

Awouters (ed.), *Proceedings, XIVth International Symposium on Medicinal Chemistry*, Maastricht, The Netherlands, Sep. 8-12, 1996, Elsevier Science B.V. (Amsterdam), (cover, front matter, table of contents, index of authors, subject index, Stanford University Libraries date stamp). Copyright 1997; date stamped Aug. 24, 1998, Swain Library, Stanford University.

Bensimon, G., et al., "A Controlled Trial of Riluzole in Amyotrophic Lateral Sclerosis," *New Engl. Med.* 330:585-591(1994).

Brown, C.M., et al., "Neuroprotective properties of Lifarizine compared with those of other agents in a mouse model of focal cerebral ischaemia," *British J. Pharmacol.* 115:1425-1432 (1995).

Catterall, W.A., "Common modes of drug action on $Na^+$ channels: Local anesthetics, antiarrhythmics and anticonvulsants," *Trends Pharmacol. Sci.* 8:57-65 (1987).

Catterall, W.A., "Neurotoxins that Act on Voltage-Sensitive Sodium Channels in Excitable Membranes," *Ann. Rev. Pharmacol. Toxicol.* 20:15-43 (1980).

Catterall, W.A., "Structure and Function of Voltage-Sensitive Ion Channels," *Science* 242:50-61 (1988).

Complaint, Civil Action No. 1:07-cv-00487 (Mar. 12, 2007).

Denicoff, K.D., et al.,"Efficacy of Carbamazepine Compared With Other Agents: A Clinical Practice Survey," *J. Clin. Psychiatry* 55:70-76 (1994).

Decision, Preliminary Motions, Bd.R. 125, interference No. 105,394 (2007).

Dimmock, J.R., et. al., "(Aryloxy)aryl Semicarbazones and Related Compounds: A Novel Class of Anticonvulsant Agents Possessing High Activity in the Maximal Electroshock Screen," *J. Med. Chem.* 39:3984-3997 (1996).

Dostert et al., "New anticonvulsants with selective MAO-B inhibitory activity," *European Neuropsychopharmacology*, 1(3):317-319 (Sep. 1991).

Elrifi et al., "Request for *ex parte* reexamination of U.S. patent No. 6,479,484 B1 ," filed Jul. 2, 2003 on behalf of Newron Pharmaceuticals, SpA.

Fariello et al, "Preclinical evaluation of PNU-151774E as a novel anticonvulsant," *J. Pharmacol. Exp. Ther.* 285(2):397-403 (May 1998).

Faravelli L. et al., "NW 1029 is a novel na+ channel blocker, with analgesic activity in animal models." Abstract, Annual Meeting, Society for Neuroscience 2000; 26 (1):1218.

Fields, "Peripheral neuropathic pain: an approach to management," in PD Wall and R Melack (eds.), *Textbook of Pain*, 3rd ed., Churchill Livingstone, pp. 991-996(1994).

(First) Declaration of Robert A. McArthur, Pevarello Exhibit 2036, interference 105,394 (2006).

First Declaration of Stephen G. Waxman, M.D., Ph.D., PX 2003, interference No. 105,394 (2006).

Galer BS, "Neuropathic pain of peripheral origin: advances in pharmacologic treatment," *Neurol*. 45:S17-S25, 1995.

Guieu et al., "Central analgesic effect of valproate in patients with epilepsy," *Seizure* 2:147-150 (1993).

Graham, S.H., et al., "Neuroprotective Effects of a Use-Dependent Blocker of Voltage-Dependent Sodium Channels, BW619C89, in Rat Middle Cerebral Artery Occlusion," *J. Pharmacol. Exp. Ther.* 269:854-859 (1994).

Hammer et al., "Effect of Riluzole on acute pain and hyperalgesia in humans," *Brit. J. Anaesthesia* 82(5):718-22 (1999).

International Search Report for PCT/EP03/12889 dated Feb. 3, 2004.

Judgment, Preliminary Motions, Bd.R. 127, interference No. 105,394 (2007).

Kingery, "A critical review of controlled clinical trials for peripheral neuropathic pain and complex regional pain syndromes," *Pain* 73:123-139 (1997).

Lunardi et al., "Clinical effectiveness of lamotrigine and plasma levels in essential and symptomatic trigeminal neuralgia," *Neurology* 48(6):1714-1717 (1997).

Magnus L., Nonepileptic uses of gabapentin experience, *Epilepsia*, 1999; 40 (Suppl. 6) S66-72; discussion 873-874.

Mathew, Ninan T., "Pathophysiology, epidemiology and impact of Migraine" *Clinical Cornerstone*, vol. 4, No. 3, 2001, pp. 1-17.

May et al., "The trigeminovascular system in humans: pathophysiologic implications for primary headache syndromes of the neural influences on the cerebral circulation," J. *Cereb. Blood flow Metab.*, vol. 9,1999, pp. 115-127.

McQuay et al., "Anticonvulsant drugs for management of pain: a systematic review," *BMJ* 311:1047-1052 (Oct. 21, 1995).

Memorandum Opinion and Order, interference No. 105,394 (2007).

Nakamura-Craig et al., "Effect of lamotrigine in the acute and chronic hyperalgesia induced by $PGE_2$ and in the chronic hyperalgesia in rats with streptozocin-induced diabetes," *Pain* 63:33-37 (1995).

Notice Of Dismissal With Prejudice, Civil Action No. 1:07-cv-00487 (Jul. 25, 2007).

Official action, counterpart Brazilian application (to RE40,259) No. PI 9814548-7 (translation), (Aug. 14, 2007).

Peitl B. et al., "Capsaicin-insenBitive sensory-efferent meningeal vasodilatation evoked by electrical stimulation of trigeminal nerve fibres in the rat," *British Journal of Pharmacology* (1999) 127, 457-467.

Pevarello et al, "Synthesis and Anticonvulsant Activity of a New Class of 2-[(Arylalkyl)amino]alkanide Derivatives", J. Med. Chem. 41:579-590 (1998).

Pevarello et al., "Stereoselectivity, sigma binding and sodium channel blocking activity of 2-amino propanamide anticonvulsants." (3 pages) (Sep. 12, 1996).

Puig et al., "Formalin-evoked activity in identified primary afferent fibers: systemic lidocaine suppresses phase-2 activity," *Pain* 64:345-355 (1995).

Reuter U. et al., Experimental models of migraine, *Functional neurology* (15) Suppl. 3 9-18, 2000.

Salvati et al. , "Anticonvulsant profile of FCE26743A (PNU-151774), a novel 2-aminopropionamide derivative. Society for Neuroscience. Washington. Nov 15-21, 1996." (4 pages) (Nov. 21, 1996, date solely for purpose of initial consideration).

Saxena et al: "Pharmacology of antimigraine drugs," *Journal of Neurology*, 1991, pp. S28-S35.

Shibata et al., "Modified formalin test: characteristic biphasic pain response," *Pain* 38:347-352 (1989).

Steiner et al: "Lamotrigine versus placebo in the prophylaxis of migraine with and without aura" *Cephalgia*, vol. 17, 1997, pp. 109-112.

Stys, P.K., et al., "Ionic Mechanism of Anoxic Injury in Mammalian CNS White Matter: Role of $Na_+$ Channels and $Na^+$-$Ca^{2+}$Exchanger," *J. Neurosci.* 12:430-439 (1992).

Supplemental data, Vieth et al., "Characteristic Physical Properties and Structural Fragments of Marketed Oral Drugs," *J. Med. Chem.* 47:224-232 (2004) (downloaded Aug. 20, 2007 from http://pubs.acs.org) (excerpted fields).

Tanelian et al., "Neuropathic pain can be relieved by drugs that are use-dependent sodium channel blockers: lidocaine, carbamazepine, and mexiletine," *Anesthesiol.* 74(5):949-951 (1991).

Tanelian et al., "Sodium channel-blocking agents: their use in neuropathic pain conditions," *Pain Forum* 4(2):75-80 (1995).

Taylor, C.P. and Meldrum, B.S., "Na$^+$ channels as targets for neuroprotective drugs," *Trends Pharmacol. Sci.* 16:309-316(1995).

Tjolsen et al., "The formalin test: an evaluation of the method," *Pain* 51:5-17 (1992).

Vaghi et al., "Neuroprotective effect of PNU-151774E, a new anticonvulsant compound, in the model of global ischaemia in gerbils." (5 pages) (Oct. 30, 1997, date solely for purpose of initial consideration).

Varasi et al., "Synthesis and anticonvulsant activity of new benzyloxybenzylacetamide derivatives," from *Abstracts, XII$^{th}$ International Symposium on Medicinal Chemistry*, Basel, Switzerland, Sep. 13-17, 1992 (2 pages) (1992).

Varasi et al., "Synthesis and anticonvulsant activity of new benzyloxybenzylacetamide derivatives" (2 pages) (1992).

Vieth et al., "Characteristic Physical Properties and Structural Fragments of Marketed Oral Drugs," *J. Med. Chem.* 47:224-232 (2004).

Webber, "Observations under article 115 EPC", filed Nov. 19, 2002 in EP 98958114.5 (EP 1032377) on behalf of Newron Pharmaceuticals, SpA.

Wenzel et al: "Migraine headache misconceptions: barriers to effective care" *Pharmacotherapy*, vol. 24, No. 5, 2004, pp. 638-648.

Wilton, "Tegretol in the treatment of diabetic neuropathy," *S. Afr. Med. J.* 48(20):869-872 (1974).

Woolf et al., "The systemic administration of local anaesthetics produces a selective depression of C-afferent fibre evoked activity in the spinal cord," *Pain* 23(4):361-374 (1985).

\* cited by examiner

ALPHA-AMINOAMIDE DERIVATIVES USEFUL AS ANTIMIGRAINE AGENTS

CROSS-REFERENCE TO RELATED APPLICATIONS

This is the U.S. national stage of International Application No. PCT/EP2003/012889, which claims the benefit of European patent application no. 03000921.1, filed Jan. 16, 2003.

The invention relates to α-aminoamide derivatives useful as antimigraine agents; particularly, the invention concerns the use of α-aminoamide derivatives in the manufacture of a medicament for the treatment of head pain conditions such as migraine, cluster headache or other severe headache.

The International Headache Classification divides head pain conditions basically into two major categories: primary and secondary headaches.

Primary headache disorders include, for instance, migraine, headache, tension type headache and cluster headache.

Secondary headache disorders result basically from other organic disturbances, such as infection, metabolic disorders, or other systemic illness.

Migraine headaches (also referred to simply as migraines) and cluster headaches are well known medical conditions. Extensive background information on them is contained in references such as "Headache in Clinical Practice" (edited by Silberstein S. et al., Oxford Univ. Press, 1998); and "Headache Disorders: A Management Guide for Practitioners", by Rapoport A. and Sheftell F. (Saunders W. B., Philadelphia, 1996). Various definitions, categories, and diagnostic standards which relate to migraine headaches (and to cluster headaches, described below, and other types of headaches as well) are defined by standardized criteria that were approved and issued by the International Headache Society (IHS), and were published as a supplement to the journal Cephalalgia in 1988.

Despite the emergence of the "triptan" drugs, known to act directly on vasoconstriction, including sumatriptan (also used to treat cluster headaches), naratriptan, zolmitriptan, and rizatriptan, there are no adequately safe, rapid, reliable, and satisfactory treatments for both primary headache disorders, such as recurrent migraines and cluster headaches, and secondary headache disorders such as the ones deriving from infection, metabolic disorders, or other systemic illnesses.

The problems and limitations that plague the treatments contemplating the use of triptans (as well as other known treatments such as, for instance, those comprising the administration of ergotamine analogs etc.) may derive from a number of causes; typically, the main drawbacks include: (i) patients with various types of cardiac or vascular problems cannot take triptan drugs safely; (ii) significant numbers of patients, who repeatedly take any single treatment, run a substantial risk of developing a form of tolerance which can lead to elevated chronic and even continuous headaches; (iii) relief often takes well over half an hour to reach appreciable levels; and (iv) immediately after a treatment, a patient often needs to rest quietly for several hours, which renders it very difficult or impossible for him or her to return to work or get anything else constructive done that day.

WO98/25594 discloses the use of 3,5-diamino-6-(2,3-dichlorophenyl)-1,2,4-triazine, an anticonvulsant also known as lamotrigine, or a pharmaceutically acceptable salt thereof, in the manufacture of a medicament for use in the treatment and/or prevention of migraine.

WO99/26614 discloses substituted 2-aminoacetamides compounds, preferably α,α'-di-substituted, for treating or ameliorating pain; in view of the activity of said compounds as blockers of sodium channels, the use thereof for the treatment of a number of diseases and conditions mediated by sodium ion influx, among which migraine headache is cited, is therein disclosed too.

It is however known that headache resulting from neurovascular mechanisms does not satisfactorily respond to treatment with analgesic agents and, conversely, antimigraine compounds, such as triptans, do not possess general analgesic properties (Steiner T. J., Findley L. J., Yuen A. W.: "Lamotrigine versus placebo in the prophylaxis of migraine with and without aura", Cephalgia 1997, 17: 109-12; Saxena P. R., Den Boer M. O.: "Pharmacology of antimigraine drugs", J. Neurology 1991, 238 Suppl. 1: S28-35); therefore, the antimigraine properties cannot be predicted on the basis of pain models.

Further, the Applicant found that representative substituted 2-aminoacetamide compounds disclosed in WO99/26614 are not effective antimigraine agents and that therefore their usefulness for the treatment of migraine and, generally speaking, of diseases and conditions mediated by sodium ion influx cannot be reasonably predicted in view of their having been recognised as blockers of sodium channels.

Given that antimigraine properties can be predicted neither on the basis of pain models nor in view of the sodium channels blocking activity of compounds, a vast medical need still exists for improved medical treatments which can provide rapid relief from the primary and secondary headaches disorders, particularly from the intense pain of acute migraine or cluster headaches, and which are not associated with problems of migraine recurrence, lingering sedation, unwanted side effects, or elevated health risks such as for patients with cardiac or vascular problems.

The main object of the present invention is to disclose and provide a rapid and highly effective method for treating primary headache disorders including migraine, such as tension type headache, transformed migraine or evolutive headache and cluster headache, as well as secondary headache disorders such as the ones deriving from infection, metabolic disorders, or other systemic illnesses and other acute headaches, in a manner which provides a highly effective treatment with virtually no adverse side effects or lingering after effects (such as drowsiness, grogginess, disorientation, nausea, or the like), thereby allowing the patient to be ready and able to drive, work, or carry out any other normal activity within an hour after such treatment is commenced.

A further object of the present invention is to disclose and provide a method for treating chronic and/or intractable pain conditions such as, f.i., trigeminal facial pain, chronic paroxysmal hemicrania and the like, resulting from a worsening of the above mentioned primary and secondary headache.

In more general terms, all types of the above mentioned headache disorders, which can be treated according to this invention, are hereinafter collectively referred to as "head pain conditions".

The word "treatment" or the expression "treatment of a condition", whenever employed in this specification, mean inhibiting such condition, i.e. either arresting its development or relieving it or causing its regression as well as preventing its development as soon as the symptoms which are characteristic of such condition begin to appear.

It has now been found that these and other objects of the invention, which will be apparent by the full reading and understanding of the following description, can be attained by the use of an α-aminoamide of formula (I):

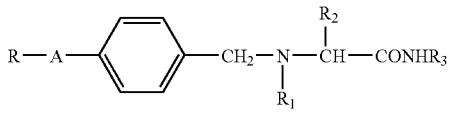

(I)

wherein:

A is a —(CH$_2$)$_m$— or —(CH$_2$)$_n$—X—, wherein m is 1 or 2; n is zero, 1 or 2; and X is —O—, —S— or —NH—;

R is a furyl, thienyl, or pyridyl ring or a phenyl ring, unsubstituted or substituted by one or two substituents independently selected from halogen, hydroxy, C$_1$-C$_4$ alkyl, C$_1$-C$_3$ alkoxy and trifluoromethyl;

R$_1$ is hydrogen or C$_1$-C$_3$ alkyl;

R$_2$ is hydrogen or C$_1$-C$_2$ alkyl, unsubstituted or substituted by hydroxy or phenyl; phenyl, unsubstituted or substituted by one or two substituents independently selected from C$_1$-C$_3$ alkyl, halogen, hydroxy, C$_1$-C$_2$ alkoxy or trifluoromethyl;

R$_3$ is hydrogen or C$_1$-C$_3$ alkyl;

if the case, either as a single isomer, or as a mixture thereof, or a pharmaceutically acceptable derivative thereof;

in the manufacture of a medicament for the treatment of head pain conditions.

The alkyl and alkoxy groups may be branched or straight chain groups. A halogen atom is preferably fluorine, chlorine or bromine, in particular fluorine or chlorine.

A C$_1$-C$_4$ alkyl is a linear or branched alkyl group; preferably a methyl, ethyl, propyl, isopropyl, butyl or terbutyl; most preferably, it is a methyl or ethyl group.

A C$_1$-C$_3$ alkoxy is a linear or branched alkoxy group; preferably a methoxy, ethoxy, propoxy, isopropoxy; most preferably, it is a methoxy or ethoxy group.

A thienyl ring is, for instance, a 2- or 3-thienyl ring.

A pyridyl ring is, for instance, a 2-, or 3- or 4-pyridyl, in particular a 3-pyridyl ring.

A furyl ring is, for instance, a 2- or 3-furyl ring.

A substituted phenyl ring is preferably substituted by one or two substituents chosen independently from halogen, C$_1$-C$_3$ alkyl and trifluoromethyl.

A C$_1$-C$_2$ alkyl group substituted by hydroxy is preferably a hydroxymethyl or 1-hydroxyethyl group.

A C$_1$-C$_2$ alkyl group substituted by a phenyl ring is preferably a benzyl or phenethyl group.

Preferably, in formula (I) above:

A is a group selected from —CH$_2$—CH$_2$—, —CH$_2$—O—, —CH$_2$—S—, —CH$_2$—CH$_2$—O—;

R is a phenyl ring, unsubstituted or substituted by one or two substituents independently selected from halogen, C$_1$-C$_3$ alkyl or a methoxy group; or a thienyl ring;

R$_1$ is hydrogen or C$_1$-C$_2$ alkyl;

R$_2$ is hydrogen or methyl, unsubstituted or substituted by hydroxy, or phenyl unsubstituted or substituted by C$_1$-C$_2$ alkyl, halogen, hydroxy, methoxy or trifluoromethyl; and R$_3$ is hydrogen or C$_1$-C$_2$ alkyl.

A further preferred group of α-aminoamides comprises the compounds of formula (I) above wherein:

A is —CH$_2$—O—, —CH$_2$—S— or —CH$_2$—CH$_2$—;

R is a phenyl ring, unsubstituted or substituted by one or two halogen atoms;

R$_1$ is hydrogen;

R$_2$ is hydrogen or methyl, unsubstituted or substituted by hydroxy or phenyl ring, unsubstituted or substituted by a halogen atom;

R$_3$ is hydrogen or methyl.

Preferred α-aminoamides for the present invention are:
2-(4-benzyloxybenzylamino)propanamide;
2-[4-(2-fluorobenzyloxy)benzylamino]propanamide;
2-[4-(2-chlorobenzyloxy)benzylamino]propanamide;
2-[4-(3-fluorobenzyloxy)benzylamino]propanamide;
2-[4-(3-chlorobenzyloxy)benzylamino]propanamide;
2-[4-(4-fluorobenzyloxy)benzylamino]propanamide;
2-[4-(2-fluorobenzyloxy)benzylamino]-N-methyl-propanamide;
2-[4-(3-fluorobenzyloxy)benzylamino]-N-methyl-propanamide;
2-[4-(2-fluorobenzyloxy)benzylamino]-3-hydroxy-propanamide;
2-[4-(3-fluorobenzyloxy)benzylamino]-3-hydroxy-propanamide;
2-(4-benzyloxybenzylamino)-3-hydroxy-N-methylpropanamide;
2-[4-(2-fluorobenzyloxy)benzylamino]-3-hydroxy-N-methylpropanamide;
2-[4-(2-chlorobenzyloxy)benzylamino]-3-hydroxy-N-methylpropanamide;
2-[4-(3-fluorobenzyloxy)benzylamino]-3-hydroxy-N-methylpropanamide;
2-[4-(3-chlorobenzyloxy)benzylamino]-3-hydroxy-N-methylpropanamide;
2-(4-(2-thienylmethylenoxy)benzylamino)-propanamide;
2-[4-(2-(3-fluorophenyl)ethyl)benzylamino]-propanamide;
2-[4-benzylthiobenzylamino]-propanamide;
2-[4-benzyloxybenzylamino]-3-phenyl-N-methylpropanamide;
2-[4-benzyloxybenzylamino]-N-methylbutanamide;
2-[4-benzyloxybenzylamino]-2-phenyl-acetamide;
2-[4-(2-fluorobenzyloxy)benzylamino]-2-phenyl-acetamide;
2-[4-(3-fluorobenzyloxy)benzylamino]-2-phenyl-acetamide;
2-[4-(3-chlorobenzyloxy)benzylamino]-2-phenyl-acetamide;
2-[4-(3-fluorobenzyloxy)benzylamino]-2-(2-fluorophenyl)-acetamide;
2-[4-(3-fluorobenzyloxy)benzylamino]-2-(3-fluorophenyl)-acetamide;
2-[4-(3-chlorobenzyloxy)benzylamino]-2-(3-fluorophenyl)-acetamide;
if the case, either as a single isomer or as a mixture thereof, or a pharmaceutically acceptable derivative thereof.

In the present invention, the following α-aminoamides are most preferred: (S)-(+)-2-[4-(3-fluorobenzyloxy)benzylamino]-propanamide (internal code and hereinafter NW-1015), (S)-(+)-2-[4-(2-fluorobenzyloxy)benzylamino]-propanamide (internal code and hereinafter NW-1029) and (S)-(+)-2-[4-(3-chlorobenzyloxy)benzylamino]-propanamide (internal code and hereinafter NW-1039).

The α-aminoamides of formula (I) and the analgesic activity thereof, in particular against chronic and neuropathic pain in mammals including humans, are disclosed in WO90/14334, WO94/22808, WO97/05102, WO99/26614, WO99/35123 and WO99/35125; any of the α-aminoamides of the above formula (I) can be prepared according to what disclosed in said documents which are herein incorporated by reference as far as the preparation of said α-aminoamides is concerned.

WO90/14334, WO94/22808, WO97/05102, WO97/05111, disclose substituted benzylaminoamide compounds active on the central nervous system and useful as anti-epileptic, anti-Parkinson, neuroprotective, antidepressant, antispastic hypnotic agents (Pevarello P., Bonsignori A., Doster P., Heidempergher F., Pinciroli V., Colombo M., McArthur R. A., Salvati P., Post C., Fariello R. G. and Varasi M.: "Synthesis and anticonvulsant activity of a new class of 2-[(arylalkyl)amino]alkanamide derivatives", J. Med. Chemistry 1998, 41: 579-590).

WO99/35123 and WO99/35125 disclose substituted benzylaminopropanamide compounds active on the central nervous system and useful as analgesic agents. It has been shown that the α-aminoamides disclosed in WO99/35123 and WO99/35125 are $Na^+$ channel blockers having analgesic effects against some models of pain in animals (Faravelli L., Maj R., Veneroni O., Fariello R. G., Benatti L., Salvati P., Society for Neuroscience 2000; 26 (1): 1218).

A further aspect of the invention relates to a method for the treatment of head pain conditions in a mammal, including humans, in need thereof comprising administering to the mammal a therapeutically effective dose of at least one α-aminoamide of formula (I) as above defined or a pharmaceutically acceptable salt thereof.

Particularly, the mammal in need of the above mentioned treatment is administered a dose of the α-aminoamide of formula (I) as above defined which ranges from about 0.05 to 20 mg/kg body weight per day; preferably in the range of about 0.5 to 10 mg/kg day; most preferably in the range of about 0.5 to 5 mg/kg day.

Head pain conditions in a mammal, including humans, can thus be inhibited, alleviated and prevented. Examples of head pain conditions in mammals which can be treated by the above defined α-aminoamide of formula (I) are those involving a cerebral vasodilatation mechanism and include both primary and secondary headache disorders; particularly, those primary headache disorders which derive from the intense pain of acute migraine or cluster headaches or from vascular mechanisms and those secondary headache disorders which derive from infection, metabolic disorders, or other systemic illnesses.

In particular, examples of head pain conditions that can be treated by the α-aminoamide of formula (I) as above defined include migraine such as, for instance, acute, transformed or vascular migraine; headache such as, for instance, acute, cluster, evolutive or tension type headache; neuralgia such as, for instance, trigeminal neuralgia; hemicrania such as, for instance, chronic paroxysmal hemicrania; facial pain and arachnoiditis.

Further, a "pharmaceutically acceptable derivative" of the α-aminoamide of formula (I) as above defined is herein meant to include any pharmaceutically acceptable metabolite, bioprecursor and/or pro-drug, i.e. a compound which has a structural formula different from the one of the α-aminoamide of formula (I) as above defined and yet is directly or indirectly converted in vivo into a compound having their structural formula, upon administration to a mammal, particularly a human being.

Examples of pharmaceutically acceptable derivatives of the α-aminoamide of formula (I) as above defined include acid addition salts with inorganic acids, e.g. nitric, hydrochloric, hydrobromic, sulphuric and phosphoric acids and the like, or organic acids, e.g. acetic, propionic, glycolic, lactic, malonic, malic, tartaric, citric, succinic, benzoic, cinnamic, mandelic, methanesulfonic, p-toluenesulfonic and salicylic acids and the like.

The α-aminoamide of formula (I) as above defined can be administered as the "active ingredient" of a pharmaceutically acceptable composition which can be prepared by conventional procedures known in the art, for instance by mixing the active ingredient with pharmaceutically acceptable, therapeutically inert organic and/or inorganic carrier materials.

The composition comprising the above defined α-aminoamide can be administered in a variety of dosage forms, e.g. orally, in the form of tablets, troches, capsules, sugar or film coated tablets, liquid solutions, emulsions or suspensions; rectally, in the form of suppositories; parenterally, e.g. by intramuscular or intravenous injection or infusion; and transdermally.

Suitable pharmaceutically acceptable, therapeutically inert organic and/or inorganic carrier materials useful in the preparation of such composition include, for example, water, gelatin, gum arabic, lactose, starch, cellulose, magnesium stearate, talc, vegetable oils polyalkyleneglycols and the like. The composition comprising the α-aminoamide of formula (I) as above defined can be sterilized and may contain further components, well known to the skilled in the art, such as, for example, preservatives, stabilizers, wetting or emulsifying agents, e.g. paraffin oil, mannide monooleate, salts to adjust osmotic pressure, buffers and the like.

For example, the solid oral forms may contain, together with the active ingredient, diluents, e.g. lactose, dextrose, saccharose, cellulose, corn starch or potato starch; lubricants, e.g. silica, talc, stearic acid, magnesium or calcium stearate, and/or polyethylene glycols; binding agents, e.g. starches, arabic gums, gelatin, methylcellulose, carboxymethylcellulose or polyvinyl pyrrolidone; disgregating agents, e.g. a starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. Said pharmaceutical preparations may be manufactured in known manner, for example, by means of mixing, granulating, tabletting, sugar-coating, or film-coating processes.

The oral formulations comprise sustained release formulations that can be prepared in conventional manner, for instance by applying an enteric coating to tablets and granules.

The liquid dispersion for oral administration may be e.g. syrups, emulsions and suspension.

The syrups may contain as carrier, for example, saccharose or saccharose with glycerine and/or mannitol and/or sorbitol.

Suspensions and emulsions may contain as a carrier, for example, a natural gum, agar, sodium alginate, pectin, methylcellulose, carboxymethylcellulose, or polyvinyl alcohol. The suspensions or solutions for intramuscular injections may contain, together with the active compound, a pharmaceutically acceptable carrier, e.g. sterile water, olive oil, ethyl oleate, glycols, e.g. propylene glycol, and, if desired, a suitable amount of lidocaine hydrochloride. The solutions for intravenous injections or infusion may contain as carrier, for example, sterile water or preferably they may be in the form of sterile, aqueous, isotonic saline solutions.

The suppositories may contain, together with the active ingredient, a pharmaceutically acceptable carrier, e.g. cocoa butter, polyethylene glycol, a polyoxyethylene sorbitan fatty acid ester surfactant or lecithin.

The composition comprising the α-aminoamide of formula (I) as above defined is generally in the form of a dose unit containing, for example, 35 to 350 mg of active ingredient per unit dosage form.

Suitable treatment is given 1, 2 or 3 times daily, depending upon clearance rate. Accordingly, the desired dose may be presented in a single dose or as divided doses administered at appropriate intervals, for example two to four or more sub-doses per day. Treatment is preferably commenced before the onset of a migraine episode and continued indefinitely.

The pharmaceutical compositions comprising the α-aminoamide of formula (I) as above defined will contain, per dosage unit, e.g., capsule, tablet, powder injection, teaspoonful, suppository and the like from about 35 to about 350 mg of the active ingredient.

Optimal therapeutically effective doses to be administered may be readily determined by those skilled in the art and will vary, basically, with the strength of the preparation, with the mode of administration and with the advancement of the condition or disorder treated. In addition, factors associated with the particular subject being treated, including subject age, weight, diet and time of administration, will result in the need to adjust the dose to an appropriate therapeutically effective level.

The advantages deriving from the use and the method of the invention as above defined are many, and include the possibility to prevent and treat basically all types of migraine, cluster or other severe headaches and to reduce or entirely stop pain caused by the headaches in a rapid and highly effective way; specifically both primary and secondary headache disorders or other systemic illnesses and other acute headaches.

Besides, the use and method of the invention should show fewer adverse side effects or lingering after effects (such as drowsiness, grogginess, disorientation, nausea, or other such problems), thereby allowing the patient to be ready and able to drive, work, or carry out any other normal activity within an hour after that such treatment is commenced.

The following examples illustrate the invention without limiting it.

EXAMPLE 1

The following pharmaceutical composition, as well as the ones of Examples 2 and 3, comprising an α-aminoamide of formula (I) as above defined, were prepared by mixing the ingredients below listed, employing methods usual in the pharmaceutical field and known to the skilled in the art.

| One 35-mg capsule contains | |
|---|---|
| NW-1015 | 35.00 mg |
| Crospovidone | 4.37 mg |
| Microcrystalline cellulose | 5.95 mg |
| Magnesium stearate | 0.17 mg |
| Colloidal silicon dioxide | 0.18 mg |

EXAMPLE 2

| One 100-mg capsule contains | |
|---|---|
| NW-1015 | 100.00 mg |
| Crospovidone | 7.50 mg |
| Microcrystalline cellulose | 8.95 mg |
| Magnesium stearate | 1.50 mg |
| Colloidal silicon dioxide | 0.30 mg |

EXAMPLE 3

| One 175-mg capsule contains | |
|---|---|
| NW-1015 | 175.00 mg |
| Crospovidone | 13.05 mg |
| Microcrystalline cellulose | 15.57 mg |
| Magnesium stearate | 2.61 mg |
| Colloidal silicon dioxide | 0.49 mg |

Pharmacology

The antimigraine activity of the above defined α-aminoamide of formula (I) has been proven by the studies reported hereinafter of vascular migraines and related disorders on animal models.

Studies [Reuter U., Sanchez del Rio M., Moskowitz M. A., "Experimental models of migraine", Functional neurology (15) Suppl. 3 9-18, 2000; Magnus L., "Nonepileptic uses of gabapentin. Experience", Epilepsia, 1999; 40 (Suppl. 6) S66-72; discussion S73-S74; Peitl B., Pethô G., Pórszász R., Németh J. and Szolcsányi J., "Capsaicin-insensitive sensory-efferent meningeal vasodilatation evoked by electrical stimulation of trigeminal nerve fibres in the rat"] of the regional cortical blood flow (CBF) have shown that during the headache phase of migraine, a dilatation of both large extra and intracranial arteries occurs. This event has been associated to an antidromic activation with a consequent vasoactive neuropeptides release, and to an orthodromic activation of the trigeminal fibers associated with an increased neuronal activity.

The above defined α-aminoamides have been found to be active in inhibiting cerebral vasodilatation evoked by electrical stimulation of ophthalmic branch of rat trigeminal ganglion and are therefore deemed to be useful as antimigraine agents.

General Methods

Animals and Surgery

Male Wistar rats (250-350 g) were anesthetized with sodium pentobarbital (50 mg/kg i.p.) dissolved in saline.

The trachea and left femoral artery were cannulated for artificial ventilation (55 strokes/min) and for measurement of mean blood pressure (MBP) respectively. The femoral vein was cannulated for the intravenous administration of test agents. Body temperature was maintained at 37-38° C. by automatic control of a heating pad.

Animals were placed in a stereotaxic frame and a longitudinal incision was made in the scalp. A burr hole was drilled in the skull and a stainless steel bipolar electrode (Plastic One MS 306) was lowered into left ophthalmic branch of the trigeminal ganglion (3.8 mm dorsal to bregma, 2.5 mm lateral from the midline and 9.5 mm below the dural surface) and secured with dental cement.

Correct placement of the electrode was confirmed by a brief electrical stimulation, which cause movement of the jaw due to activation of the trigeminal fiber. Following removal of the brain, the correct position of the electrode into the fiber, was visually checked at the end of each experiment.

A second hole was drilled ipsilateral of the electrode (1.5 mm rostral to bregma, and 1.5 mm lateral from the sagittal suture) and a needle probe (tip diameter 0.8 mm) of a laser doppler flowmeter was fixed pointing with its tip onto a branch of the middle cerebral artery (MCA) and Cerebral Blood Flow (CBF) change recorded on-line by the PeriFlux 4001 Laser Doppler system.

Artefacts of the laser Doppler reading during electrical stimulation of the trigeminal ganglion due to muscular movements were prevented by a bolus of i.v. injection of the neuromuscular blocker pancuronium bromide (0.6 mg/kg i.v.). Anesthesia and neuromuscular blockade were maintained all over the experiment with an infusion of sodium pentobarbital and pancuronium (12.5 mg/kg/h+2.4 mg/kg/h, respectively).

Experimental Protocol

At the end of the surgery, a pause of thirty minutes was taken in order to stabilize the measured parameters.

Rest CBF was increased by electrical stimulation with rectangular pulse of 0.5 msec length, 1-10 Hz, 0.5-1 mA for periods of 30 seconds. After two averaged pre-drug stimulations, vehicle or drugs were administered.

The α-aminoamide compounds NW-1015, NW-1029, NW-1039, representative of the invention, and the comparative 2-(4-(2-fluorobenzyloxy)benzylamino)-2-methyl-propanamide (internal code and hereinafter NW1050), 2-(4-(4-fluorobenzyloxy)benzylamino)-2-methyl-propanamide (internal code and hereinafter NW1055, also one of the compounds tested in WO99/26614), 4-(4'-fluorophenoxy)-benzaldheyde semicarbazone (hereinafter Co102862, tested in WO00/61188) and vehicle, were administered intravenously after second basal stimulation registering the responses to evoked flow by electrical stimulation at 5, 15, 30 and 60 min after treatment.

NW-1015, was administered at the doses of 1, 2 and 5 mg/kg; NW-1029 was administered at the doses of 5 and 10 mg/kg and NW-1039 at the doses of 2 and 5 mg/kg whereas NW-1050, NW-1055 and Co102862 were all administered at the dose of 20 mg/kg.

The responses obtained after drug administration were compared to the vehicle group, and were reported as a percentage of the inhibition of the evoked CBF. Data were compared by analysis of covariance (ANCOVA) followed by Dunnet's test.

Results

The antimigraine effect of the tested compounds was observed and measured as the percentage of the inhibition after i.v. administration of the above mentioned representative compounds of the CBF evoked in control condition. The data reported in table 1 below show the inhibitory activity of the tested compounds on the CBF response evoked by electrical stimulation of the left ophthalmic branch of the trigeminal ganglion.

TABLE 1

| Compound | Dose (mg/kg) | Time (min) after administration % Inhibition of the CBF response | | | |
|---|---|---|---|---|---|
| | | 5 | 15 | 30 | 60 |
| NW-1015 | 1 | 25.6 ± 2.9 | 25.8 ± 2.7 | 36.6 ± 4.7** | 15.7 ± 9.8 |
| NW-1015 | 2 | 15.0 ± 1.8* | 22.0 ± 3.8** | 20.6 ± 6.2* | 4.0 ± 6.3 |
| NW-1015 | 5 | 25.2 ± 2.6 | 35.5 ± 6.5** | 34.7 ± 1.9** | 27.1 ± 3.6 |
| NW-1029 | 5 | 15.5 ± 3.7 | 20.8 ± 3.5 | 27.8 ± 3.9** | 30.6 ± 2.8 |
| NW-1029 | 10 | 23.9 ± 3.9 | 34.9 ± 8.2** | 35.3 ± 2.6** | 35.7 ± 3.9** |
| NW-1039 | 2 | 24.2 ± 6.2 | 31.3 ± 6.2* | 32.1 ± 8.1** | 36.2 ± 9.1** |
| NW-1039 | 5 | 45.0 ± 6.3** | 41.7 ± 1.8** | 38.1 ± 2.6** | 20.9 ± 9.4 |
| NW-1050 | 20 | 1.2 ± 0.3 | 1.8 ± 0.6 | 1.7 ± 0.8 | 0.9 ± 0.1 |
| NW-1055 | 20 | 6.9 ± 4.2 | 3.4 ± 3.2 | 11.3 ± 2.0 | 14.0 ± 4.0 |
| Co102862 | 20 | 0.9 ± 0.1 | 1.1 ± 0.3 | 1.2 ± 0.2 | 0.7 ± 0.1 |

*p < 0.05,
**p < 0.01 by Dunnett's t test

Results (mean±S.E. of 4/6 rats per group) are expressed as percent of the inhibition on evoked CBF response versus the vehicle.

NW-1015 showed a long lasting i.v. activity reducing the evoked CBF up to 60 min after administration. NW-1029 equally, reduced the evoked CBF compared to the vehicle up to 60 min post administration. NW-1039 at the doses tested produced a decrease of the evoked CBF response compared to the vehicle group.

NW-1055 at 20 mg/kg caused a light inhibition of the evoked CBF, which however did not reach a statistically significant difference in comparison with the vehicle treated group. NW-1050 and Co102862 at 20 mg/kg were completely inactive.

The above data confirm that representative substituted 2-aminoacetamides compounds disclosed in WO99/26614 are not effective as antimigraine agents and that therefore such activity cannot be reasonably predicted in view of having recognised such compounds as blockers of sodium channels. Particularly, the preferred α,α'-di-substituted acetamides (2-methylpropanamide derivatives) showed a far lower potency than the above defined amides of formula (I).

The above biological activities confirm that the α-aminoamide of formula (I) as above defined can be used as antimigraine agents, in particular, to treat head pain conditions which involve a cerebral vasodilatation mechanism.

The invention claimed is:

1. A method of treating migraine, comprising: administering to a mammal having a migraine a therapeutically effective amount of an α-aminoamide of formula (I):

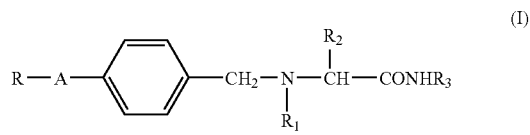

(I)

wherein:

A is a or —$(CH_2)_m$— or —$(CH_2)_n$—X—, wherein m is 1 or 2; n is zero, 1 or 2; and X is —O—, —S— or —NH—;

R is a phenyl ring, unsubstituted or substituted by one or two substituents independently selected from halogen, hydroxy, $C_1$-$C_4$ alkyl, $C_1$-$C_3$ alkoxy and trifluoromethyl;

$R_1$ is hydrogen or $C_1$-$C_3$ alkyl;

$R_2$ is hydrogen or $C_1$-$C_2$ alkyl, unsubstituted or substituted by hydroxy or phenyl; phenyl, unsubstituted or substituted by one or two substituents independently selected from $C_1$-$C_3$ alkyl, halogen, hydroxy, $C_1$-$C_2$ alkoxy or trifluoromethyl;

$R_3$ is hydrogen or $C_1$-$C_3$ alkyl;

or an optically active isomer, racemic mixture, or pharmaceutically acceptable derivative thereof.

2. A method according to claim 1, wherein in formula (I):
A is a group selected from —$CH_2$—$CH_2$—, —$CH_2$—O—, —$CH_2$—S—, —$CH_2$—$CH_2$—O—;

R is a phenyl ring, unsubstituted or substituted by one or two substituents independently selected from halogen, $C_1$-$C_3$ alkyl or a methoxy group; or a thienyl ring;

$R_1$ is hydrogen or $C_1$-$C_2$ alkyl;

$R_2$ is hydrogen or methyl, unsubstituted or substituted by hydroxy, or phenyl unsubstituted or substituted by $C_1$-$C_2$ alkyl, halogen, hydroxy, methoxy or trifluoromethyl; and $R_3$ is hydrogen or $C_1$-$C_2$ alkyl.

3. A method according to claim 1, wherein in formula (I):

A is —$CH_2$—O—, —$CH_2$—S— or —$CH_2$—$CH_2$—;

R is a phenyl ring, unsubstituted or substituted by one or two halogen atoms;

$R_1$ is hydrogen;

$R_2$ is hydrogen or methyl, unsubstituted or substituted by hydroxy or phenyl ring, unsubstituted or substituted by a halogen atom; and $R_3$ is hydrogen or methyl.

4. A method according to claim 1, wherein the α-aminoamide is selected from the group consisting of:

2-(4-benzyloxybenzylamino)propanamide;
2-[4-(2-fluorobenzyloxy)benzylamino]propanamide;
2-[4-(2-chlorobenzyloxy)benzylamino]propanamide;
2-[4-(3-fluorobenzyloxy)benzylamino]propanamide;
2-[4-(3-chlorobenzyloxy)benzylamino]propanamide;
2-[4-(4-fluorobenzyloxy)benzylamino]propanamide;
2-[4-(2-fluorobenzyloxy)benzylamino]-N-methyl-propanamide;
2-[4-(3-fluorobenzyloxy)benzylamino]-N-methyl-propanamide;
2-[4-(2-fluorobenzyloxy)benzylamino]-3-hydroxy-propanamide;
2-[4-(3-fluorobenzyloxy)benzylamino]-3-hydroxy-propanamide;
2-(4-benzyloxybenzylamino)-3-hydroxy-N-methylpropanamide;
2-[4-(2-fluorobenzyloxy)benzylamino]-3-hydroxy-N-methylpropanamide;
2-[4-(2-chlorobenzyloxy)benzylamino]-3-hydroxy-N-methylpropanamide;
2-[4-(3-fluorobenzyloxy)benzylamino]-3-hydroxy-N-methylpropanamide;
2-[4-(3-chlorobenzyloxy)benzylamino]-3-hydroxy-N-methylpropanamide;
2-[4-(2-(3-fluorophenyl)ethyl)benzylamino)-propanamide;
2-[4-benzylthiobenzylamino)-propanamide;
2-[4-benzyloxybenzylamino]-3-phenyl-N-methylpropanamide;
2-[4-benzyloxybenzylamino]-N-methylbutanamide;
2-[4-benzyloxybenzylamino]-2-phenyl-acetamide;
2-[4-(2-fluorobenzyloxy)benzylamino]-2-phenyl-acetamide;
2-[4-(3-fluorobenzyloxy)benzylamino]-2-phenyl-acetamide;
2-[4-(3-chlorobenzyloxy)benzylamino]-2-phenyl-acetamide;
2-[4-(3 fluorobenzyloxy)benzylamino]-2-(2-fluorophenyl)-acetamide;
2-[4-(3-fluorobenzyloxy)benzylamino]-2-(3-fluorophenyl)-acetamide; and
2-[4-(3-chlorobenzyloxy)benzylamino]-2-(3-fluorophenyl)-acetamide;

or an optically active isomer, racemic mixture, or pharmaceutically acceptable derivative thereof.

5. A method according to claim 1, wherein the α-aminoamide is selected from the group consisting of:

(S)-(+)-2[4-(3-fluorobenzyloxy)benzylamino]-propanamide,
(S)-(+)-2-[4-(2-fluorobenzyloxy)benzylamino]-propanamide and
(S)-(+)-2-[4-(3-chlorobenzyloxy)benzylamino]-propanamide.

6. A method according to claim 1, wherein said migraine is migraine with visual aura.

7. The method of claim 1, wherein the therapeutically effective amount is from about 0.05 to 20 mg/kg body weight per day.

8. The method of claim 1, wherein the therapeutically effective amount is from about 0.5 to 10 mg/kg day.

9. A method of claim 1, wherein the therapeutically effective amount is from about 0.5 to 5 mg/kg day.

10. The method of claim 5, wherein said α-aminoamide is (S)-(+)-2-[4-(3-fluorobenzyloxy)benzylamino]-propanamide.

11. The method of claim 5, wherein said α-aminoamide is (S)-(+)-2-[4-(2-fluorobenzyloxy)benzylamino]-propanamide.

12. The method of claim 5, wherein said α-aminoamide is (S)-(+)-2-[4-(3-chlorobenzyloxy)benzylamino]-propanamide.

13. The method of claim 5, wherein the mammal is a human.

14. The method of claim 5, wherein the pharmaceutically acceptable derivative is an acid addition salt.

15. The method of claim 5, wherein said administering is by oral administration.

16. The method of claim 5, wherein said administering is by parenteral administration.

* * * * *